US011931142B1

(12) United States Patent
Brockway et al.

(10) Patent No.: US 11,931,142 B1
(45) Date of Patent: Mar. 19, 2024

(54) APNEIC/HYPOPNEIC ASSESSMENT VIA PHYSIOLOGICAL SIGNALS

(71) Applicant: VivaQuant Inc., Arden Hills, MN (US)

(72) Inventors: Marina Brockway, St. Paul, MN (US); Brian Brockway, St. Paul, MN (US); Daniel Jiang Stein, Saint Paul, MN (US)

(73) Assignee: VIVAQUANT, Inc, Arden Hills, MN (US)

( * ) Notice: Subject to any disclaimer, the term of this patent is extended or adjusted under 35 U.S.C. 154(b) by 848 days.

(21) Appl. No.: 16/824,354

(22) Filed: Mar. 19, 2020

Related U.S. Application Data

(60) Provisional application No. 62/820,530, filed on Mar. 19, 2019.

(51) Int. Cl.
A61B 5/08 (2006.01)
A61B 5/00 (2006.01)
(Continued)

(52) U.S. Cl.
CPC .......... A61B 5/0826 (2013.01); A61B 5/0022 (2013.01); A61B 5/0024 (2013.01);
(Continued)

(58) Field of Classification Search
CPC ..... A61B 5/0826; A61B 5/349; A61B 5/0022; A61B 5/0024; A61B 5/0205;
(Continued)

(56) References Cited

U.S. PATENT DOCUMENTS 5,090,418 A 2/1992 Squires et al.
5,279,283 A 1/1994 Dillon
(Continued)

FOREIGN PATENT DOCUMENTS

JP 3787336 B2 * 6/2006 ......... A61B 5/02416
JP 2012 045304 A 3/2012
(Continued)

OTHER PUBLICATIONS

Machine Translation of JP-3787336, Patent Translate, pp. 1-29, printed on Jan. 6, 2022 (Year: 2006).*
(Continued)

Primary Examiner — Matthew Kremer
Assistant Examiner — Om Patel
(74) Attorney, Agent, or Firm — Crawford Maunu PLLC

(57) ABSTRACT

Aspects of the present disclosure are directed to detecting apneic and/or hypopneic events, utilizing a physiological signal. Various apparatuses and/or methods involve computing time series of interbeat intervals are from data characterizing activity of a beating heart, decomposing the time series is into subcomponents, and identifying ones of the subcomponents that relate to a portion of the data during which an apneic and/or hypopneic, as may be detected via oximetry. Once identified, these subcomponents and related formula/weighting can be utilized in computing further subcomponents from the data, and identifying further apneic and/or hypopneic events therefrom. In this context, such events may be detected without necessarily involving further use of oximetry.

13 Claims, 6 Drawing Sheets

(51) Int. Cl.
*A61B 5/0205* (2006.01)
*A61B 5/349* (2021.01)

(52) U.S. Cl.
CPC .......... *A61B 5/0205* (2013.01); *A61B 5/349* (2021.01); *A61B 5/6801* (2013.01); *A61B 5/726* (2013.01); *A61B 5/7282* (2013.01); *A61B 2562/0219* (2013.01)

(58) Field of Classification Search
CPC ..... A61B 5/6801; A61B 5/726; A61B 5/7282; A61B 2562/0219
See application file for complete search history.

(56) References Cited

U.S. PATENT DOCUMENTS

| | | |
|---|---|---|
| 5,313,953 A | 5/1994 | Yomtov et al. |
| 5,331,959 A | 7/1994 | Imran |
| 5,521,851 A | 5/1996 | Wei et al. |
| 5,776,073 A | 7/1998 | Garfield et al. |
| 5,792,065 A | 8/1998 | Xue et al. |
| 5,817,027 A | 10/1998 | Arand et al. |
| 5,827,195 A | 10/1998 | Lander |
| 5,987,352 A | 11/1999 | Klein et al. |
| 6,117,077 A | 9/2000 | Del Mar et al. |
| 6,389,308 B1 | 5/2002 | Shusterman |
| 6,589,189 B2 | 7/2003 | Meyerson et al. |
| 6,690,959 B2 | 2/2004 | Thompson |
| 6,701,170 B2 | 3/2004 | Stetson |
| 6,775,571 B1 | 8/2004 | Kroll |
| 6,821,256 B2 | 11/2004 | Ackerman et al. |
| 6,822,564 B2 | 11/2004 | Ai-Ali |
| 6,856,832 B1 | 2/2005 | Matsumura et al. |
| 7,096,060 B2 | 8/2006 | Arand et al. |
| 7,099,714 B2 | 8/2006 | Houben |
| 7,115,096 B2 | 10/2006 | Siejko et al. |
| 7,236,819 B2 | 6/2007 | Brockway et al. |
| 7,272,265 B2 | 9/2007 | Kouri et al. |
| 7,376,453 B1 | 5/2008 | Diab et al. |
| 7,395,114 B2 | 7/2008 | Czygan et al. |
| 7,480,529 B2 | 1/2009 | Li |
| 7,602,985 B2 | 10/2009 | Gao et al. |
| 7,627,369 B2 | 12/2009 | Hunt |
| 7,672,717 B1 | 3/2010 | Zikov et al. |
| 7,840,259 B2 | 11/2010 | Xue et al. |
| 7,846,104 B2 | 12/2010 | MacQuarrie et al. |
| 7,966,067 B2 | 6/2011 | Rousso et al. |
| 8,086,304 B2 | 12/2011 | Brockway et al. |
| 8,201,330 B1 | 6/2012 | Rood et al. |
| 8,214,007 B2 | 7/2012 | Baker et al. |
| 8,271,073 B2 | 9/2012 | Zhang et al. |
| 8,348,852 B2 | 1/2013 | Bauer et al. |
| 8,433,395 B1 | 4/2013 | Brockway et al. |
| 8,460,189 B2 | 6/2013 | Libbus et al. |
| 8,478,389 B1 | 7/2013 | Brockway et al. |
| 8,543,195 B1 | 9/2013 | Brockway et al. |
| 8,588,908 B2 | 11/2013 | Moorman et al. |
| 8,608,984 B1 | 12/2013 | Taranekar et al. |
| 8,632,465 B1 | 1/2014 | Brockway |
| 8,755,876 B2 | 6/2014 | Chon et al. |
| 9,037,477 B2 | 5/2015 | Bardy et al. |
| 9,095,266 B1 | 8/2015 | Fu |
| 9,314,181 B2 | 4/2016 | Brockway et al. |
| 9,408,549 B2 | 8/2016 | Brockway et al. |
| 2002/0077536 A1 | 6/2002 | Diab et al. |
| 2003/0185408 A1 | 10/2003 | Causevic et al. |
| 2003/0236447 A1 | 12/2003 | Ritland |
| 2004/0111141 A1 | 6/2004 | Brabec et al. |
| 2004/0138578 A1 | 7/2004 | Pineda et al. |
| 2004/0167417 A1 | 8/2004 | Schulhauser et al. |
| 2005/0010120 A1 | 1/2005 | Jung et al. |
| 2005/0075708 A1 | 4/2005 | O'Brien et al. |
| 2005/0203604 A1 | 9/2005 | Brabec et al. |
| 2005/0234361 A1 | 10/2005 | Holland |
| 2005/0265629 A1 | 12/2005 | Fu et al. |
| 2005/0283090 A1 | 12/2005 | Wells |
| 2006/0094992 A1 | 5/2006 | Imboden et al. |
| 2006/0149144 A1* | 7/2006 | Lynn ..................... A61B 5/145 600/323 |
| 2007/0060815 A1 | 3/2007 | Martin et al. |
| 2007/0219453 A1 | 9/2007 | Kremliovsky et al. |
| 2007/0219455 A1 | 9/2007 | Wong et al. |
| 2007/0260151 A1 | 11/2007 | Clifford |
| 2007/0265508 A1 | 11/2007 | Sheikhzadeh-Nadjar |
| 2008/0065158 A1 | 3/2008 | Ben-Ezra et al. |
| 2008/0097280 A1 | 4/2008 | Martin et al. |
| 2008/0097537 A1 | 4/2008 | Duann et al. |
| 2008/0183093 A1 | 7/2008 | Duann et al. |
| 2008/0195169 A1 | 8/2008 | Pinter et al. |
| 2008/0200832 A1 | 8/2008 | Stone |
| 2008/0228094 A1 | 9/2008 | Audet et al. |
| 2008/0255464 A1 | 10/2008 | Vincent |
| 2008/0287770 A1 | 11/2008 | Kurzweil et al. |
| 2009/0069703 A1 | 3/2009 | Takla et al. |
| 2009/0222262 A1 | 9/2009 | Kim et al. |
| 2010/0056940 A1 | 3/2010 | Moorman et al. |
| 2010/0063438 A1 | 3/2010 | Bengtsson |
| 2010/0234916 A1 | 9/2010 | Turcott et al. |
| 2011/0046461 A1 | 2/2011 | McKenna |
| 2011/0046498 A1* | 2/2011 | Klap ..................... A61B 5/6887 600/534 |
| 2011/0152957 A1 | 6/2011 | Shaquer |
| 2011/0190648 A1 | 8/2011 | Gu et al. |
| 2011/0306895 A1 | 12/2011 | Nakashima et al. |
| 2012/0165691 A1 | 6/2012 | Ting et al. |
| 2012/0197144 A1 | 8/2012 | Christ et al. |
| 2012/0232417 A1 | 9/2012 | Zhang |
| 2013/0019383 A1 | 1/2013 | Korkala et al. |
| 2013/0069768 A1 | 3/2013 | Madhyastha et al. |
| 2013/0109937 A1 | 5/2013 | Banet et al. |
| 2013/0289424 A1 | 10/2013 | Brockway et al. |
| 2014/0005988 A1* | 1/2014 | Brockway .......... H03H 17/0248 703/2 |
| 2014/0135608 A1 | 5/2014 | Gazzoni et al. |
| 2014/0180597 A1 | 6/2014 | Brown |
| 2018/0344241 A1* | 12/2018 | Höskuldsson ..... A61B 5/02416 |

FOREIGN PATENT DOCUMENTS

| | | | |
|---|---|---|---|
| WO | WO-2005018737 A1 * | 3/2005 | ............... A61B 5/00 |
| WO | WO-2005030048 A1 * | 4/2005 | ............... A61B 5/00 |
| WO | 2006/044699 A2 | 4/2006 | |
| WO | WO-2007143535 A2 * | 12/2007 | ........... A61B 5/0205 |
| WO | 2013/043157 A2 | 3/2013 | |
| WO | 2014/123512 A1 | 8/2014 | |

OTHER PUBLICATIONS

Pan et al., "Accurate Removal of Baseline Wander in ECG Using Empirical Mode Decomposition" Proceedings of NFSI & ICFBI; pp. 177-180 (2007).
http://www.simplehelp.net/2006/09/12/how-to-set-up-outlook-2003-for-email/.
Lee, J., "Time-Varying Coherence Function for Atrial Fibrillation Detection". IEEE Transactions on Miomedical Engineering vol. 60, No. 10, Oct. 2013.
C. Li, C. Zheng, and C. Tai, "Detection of ECG characteristic points using wavelet transforms," IEEE Trans. Biomed. Eng., vol. 42, pp. 21-28, 1995.
V.X. Afonso, W.J. Tompkins, T.Q. Nguyen, and S. Luo, "ECG beat detection using filter banks," IEEE Trans. Biomed. Eng., vol. 46, pp. 192-202, 1999.
Z. Dokur, T. Olmez, E. Yazgan, and O.K. Ersoy, "Detection of ECG waveforms by neural networks," Med. Eng. Phys., vol. 19, No. 8, pp. 738-741, 1997.
Paul S Addison. Wavelet transforms and the ECG: a review. Physiol. Meas. 26 (2005) R155-R199.
JS. Sahambi', S.N. Tandonz5 R.K.P. Bhatt. Using Wavelet Transforms for ECG Characterization. IEEE Engineering in Medicine and Biology, Jan./Feb. 1997.
Beck et al., "An Inventory for Measuring Depression", Arch Gen

(56) References Cited

OTHER PUBLICATIONS

Psychiatry, 4:561-571 (Jun. 1961).
Galinier et al., "Depressed low frequency power of heart rate variability as an independent predictor of sudden death in chronic heart failure", Eur. Hrt. J., 21:475-482. (2000).
Ghasemi et al., "A Semi-Automated QT Interval Measurement Based on Wavelet and Energy Analysis," http://physionet.org/challenge/2006/papers.
Pincus, "Approximate entropy as a measure of system complexity", Proc Natl Acad Sci USA, 88:2297-2301 (Mar. 1991).
Quintana et al., "Considerations in the assessment of heart rate variability in biobehavioral research", Frontiers in Physiology, 5(805):1-10 (Jul. 22, 2014).
Sadabadi et al., "A mathematical algorithm for ECG signal denoising using window analysis," Biomed Pap Med Fac Univ Palacky Olomouc Czechoslovakia., 151(1):73-8 (Jul. 2007).
Woo et al., "Patterns of beat-to-beat heart rate variability in advanced heart failure", Am Heart J., 123:704-710 (Apr. 1992).
Igarashi et al., "The Appearance of Human Skin" Technical Report: CUCS-024-05, Dept. of Comp. Sci., Columbia Univ. NY (2005).
Allen et al., "Honey Carbon: a Review of Graphene" 30 Chem. Rev. 110:132-145 (2010).
Cuiwei et al., "Detection of ECG characteristic points using wavelet transforms." Biomedical Engineering, IEEE Transactions on 42(1):21-28 (Jan. 1995). (Abstract).
Figueredo et al., "Compression of Electrocardiogram Using Neural Networks and Wavelets," Computer and Information Science Studies in Computational Intelligence, 131:27-40 (2008).
Billmang, "Heart Rate Variability? A Historical Perspective." Frontiers in Physiology (Nov. 29, 2011).
Boerma et al., "Disparity between skin perfusion and sublingual microcirculatory alterations in severe sepsis and septic shock: a prospective observational study." Intensive Care Med., 1294-1298 (2008).
Bramwell et al., The Velocity of the Pulse Wave in Man, Proceedings of the Royal Society of London: Biological Sciences, 93:298-306 (1922).
Buller et al., "Estimation of human core temperature from sequential heart rate observations," Physiological Measurement 34:781-798 (2013).
Cooke et al., "Heart rate variability and its association with mortality in prehospital trauma patients." J Trauma, 363-370 (2006).
Ezri et al., "Pulse Oximetry from the Nasal Septum." Journal of Clinical Anesthesia. 3.6:447-450 (1991).
Griffin et al., Heart rate characteristics and laboratory tests in neonatal sepsis. Pediatrics, A115(4):937-941 (2005).
Joly et al., "Temperature of the great toe as an indication of the severity of shock." Circulation, 131-8 (1969).
Morey et al., "Feasibility and Accuracy of Nasal Alar Pulse Oximetry." British Journal of Anaesthesia. 112.6:1109-1114 (2014).
Wang et al., "Optimal Depth for Nasopharyngeal Temperature Probe Positioning," Anesthesia and Analgesia. 122.5: 1434-8 (2016).
G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).
T. Blaschke and L. Wiskott, "Cubica: Independent Component Analysis By Simultaneous Third- and Fourth-Order Cumulant Diagonalization," IEEE Transactions on Signal Processing, vol. 52, No. 5, pp. 1250-1256 (May 2004).
D A Clunie, "Extension of an open source DICOM toolkit to support SCP-ECG waveforms," 2nd OpenECG Workshop 2004, Berlin, Germany.
J.-P Martinez, et al., "A wavelet-based ECG delineator: Evaluation on standard databases," IEEE transactions on biomedical engineering, vol. 51, No. 4, pp. 57 (2004).
Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.
Costa.et. al., "Multiscale entropy analysis of biological signals," Physical Review E 71, 021906:1-18 (2005).
M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).
S.-C. Tai, C.-C. Sun and W.- C Yan, "2-D ECG Compression Method Based on Wavelet Transform and Modified SPIHT," IEEE Trans. Biomed. Eng., vol. 52, No. 6, pp. 999-1008 (Jun. 2005).
Hamlin RL. Non-drug-related electrocardiogram animal models in safety pharmacology. J Pharmacol Toxicol Methods. Jul.-Aug. 2005; 52(1): 60-76.
Van der Linde et al., "A new method to calculate the beat-to-beat instability of QT duration in drug-induced long QT in anesthetized dogs," Journal of Pharmacological and Toxicological Methods 52:168-177 (2005).
R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).
M. Blanco-Velasco, B. Weng and KE Barner, "A New ECG Enhancement Algorithm for Stress ECG Tests," Computers in Cardiology, vol. 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.- M Poggi, "Multivariate de-noising using wavelets and principal component analysis," Computational Statistics & Data Analysis, 50, pp. 2381-2398 (2006).
Aharon, M. Elad and A. Bruckstein, "K-SVD: an Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology. vol 5, pp. 667-677. 2006.
Inan et al. "Robust Neural-Network-Based Classification of Premature Ventricular Contractions Using Wavelet Transform and Timing Interval Features," IEEE Transactions on Biomedical Engineering, 53(12-1):2507-2515 (Dec. 2006). (Abstract).
Smith, "A tutorial on Principal Components Analysis" (Feb. 26, 2002).
Ueno, et al., "Capacitive sensing of electrocardiographic potential through cloth from the dorsal surface of the body in a supine position: a preliminary study," IEEE Transactions on Biomedical Engineering, 54(4):759-766 (Apr. 2007).
K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).
X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).
Schimpf et al., "Electromechanical coupling in patients with the short QT syndrome: Further insights into the mechanoelectrical hypothesis of the U wave," Heart Rhythm Society, 5(2): 241-245 (Feb. 2008).

(56) References Cited

OTHER PUBLICATIONS

Sarkar et al., "A detector for a chronic implantable atrial tachyarrhythmia monitor," IEEE Trans Biomed Eng., 55(3):1219-1224 (Mar. 2008). (Abstract).
M. Malik, K. Hnatkova, T. Novotny, G Schmidt Subject-specific profiles of QT/RR hysteresis. Am J Physiol Heart Circ Physiol 295:H2356-H2363, 2008.
Akturk et al, "Electron transport and full-band electron phonon interactions in graphene," J. of Applied Physics 103 (2008). (Abstract).
Paredes et al., "Atrial Activity Detection through a Sparse Decomposition Technique," 2:358-362, IBMEI '08 Proceedings of the 2008 International Conference on BioMedical Engineering and Informatics May 27-30, 2008, 2:358-362 (2008). (Abstract).
R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).
O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).
Li et al., "Multiresolution Subband Blind Source Separation: Models and Methods," Journal of Computers, 4(7): 681-688 (Jul. 2009).
Afonso et al., Detecting ventricular fibrillation. IEEE Engineering in Medicine and Biology Magazine, vol. 14(2):152-159 (Mar./Apr. 1995).
Dash et al., "Automatic real time detection of atrial fibrillation," Ann Biomed Eng., 37(9):1701-1709. Epub Jun. 17, 2009. (Sep. 2009). (Abstract).
M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).
R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).
Piccini, et al, "Predictors of sudden cardiac death change with time after myocardial infarction: results from the VALIANT trial," European Heart Journal 2010 31(2):211-221 (Oct. 23, 2009).
J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).
Hadei et al., "A Family of Adaptive Filter Algorithms in Noise Cancellation for Speech Enhancement," International Journal of Computer and Electrical Engineering, 2(2):1793-8163 (Apr. 2010).
Allen et al.,"Honeycomb Carbon: a Review of Graphene" Chem. Rev. 110:132-145.(2010).
Attila S. Farkas. et. al. Biomarkers and endogenous determinants of dofetilide-induced torsades de pointes in α1-adrenoceptor-stimulated, anaesthetized rabbits. British Journal of Pharmacology. vol 161, Issue 7, pp. 1477-1495, Dec. 2010.
Van der Linde et al, "The Electro-Mechanical window: a risk marker for Torsade de Pointes in a canine model of drug induced arrhythmias: ElectroMechanical window and FEAB model," British Journal of Pharmacology 161:1444-1454 (2010).
Daubechies et al., "Synchrosqueezed wavelet transforms: an empirical mode decomposition-like tool," Applied and Computational Harmonic Analysis, 30(2):243-261 (Mar. 2011).
Brockway et al., "Evaluation of an algorithm for highly automated measurements of QT interval," Journal of Pharmacological and Toxicological Methods, 64(1):16-24 (Jul./Aug. 2011). (Abstract).
PhysioBank Archive Indix from PhysioNet, the research resource for complex physiologic signals. http://www.physionet.org/physiobank/database/#ecg (downloaded on Aug. 12, 2014).
MIT-BIH Arrhythmia Database from PhysioNet, the research resource for complex physiologic signals. http://www.physionet.org/physiobank/database/mitdb/ (downloaded on Aug. 12, 2014). This database is described in: Moody et al., "The impact of the MIT-BIH Arrhythmia Database" IEEE Eng in Med and Biol, 20(3):45-50 (May-Jun. 2011). (PMID: 11446209).
Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.
Kellermann, et al.,"A mobile phone based alarm system for supervising vital parameters in free moving rats," BMC Research Notes 2012, 5:119, Feb. 23, 2012.
Widrow, et al., "Adaptive noise cancelling: principles and applications," IEEE Proc., 63(12):1692-1716 (Dec. 1975).
Boudoulas et al., "The QT greater that QS2 syndrome: a new mortality risk indicator in coronary artery disease," American Journal of Cardiology, 50(6):1229-1235 (Dec. 1982).
Moody et al., "A noise stress test for arrhythmia detectors," Computers in Cardiology, 11:381-384 (1984).
Rao et al, "Discrete Cosine Transform: Algorithms, Advantages, Applications," San Diego, CA: Academic (1990).
J. Woods. Subband Coding, Kluwer Academic Press (1990).
Ball et al., "Dynamical Eigenfunction Decomposition of Turbulent Channel Flow," International Journal for Numerical Methods in Fluids, 12(6):585-604 (Apr. 1991).
Thakor et al., "Applications of adaptive filtering to ECG analysis: noise cancellation," IEEE Transactions on Biomedical Engineering, 38(8):785-794 (Aug. 1991).
Mallat et al., "Singularity Detection and Processing with Wavelets," IEEE Transactions on Information Technology 38:617-643 (1992).
Mallat et al., "Characterization of Signals from Multiscale Edges," IEEE Trans. Pattern Analysis and Machine Intelligence, 14(7):710-732 (Jul. 1992).
Vaidyanathan, "Multirate Systems and Filter Banks," Prentice Hall, Englewood Cliffs, 1993.
Pati et al., "Orthogonal Matching Pursuit: Recursive Function Approximation With Applications to Wavelet Decomposition," in Asilomar Conference on Signals, Systems and Computers, 1:40-44 (Nov. 1993).
Mallat et al., "Matching Pursuits with Time-Frequency Dictionaries," IEEE Transactions on Signal Processing, 41(12):3397-3415 (Dec. 1993).
Comon, "Independent component analysis, a new concept?," Signal Process. Special Issue on Higher Order Statistics, 36(3):287-314 (Apr. 1994).
Donoho et al., "Ideal spatial adaptation by wavelet shrinkage," Biometrika, 81(3):425-455 (1994).
Xu et al., "Wavelet Transform Domain Filters: a Spatially Selective Noise Filtration Technique," IEEE Transactions on Image Processing, 3(6):747-758 (1994).
Donoho, "Denoising by Soft-Thresholding," IEEE Trans. on Inf. Theory, 41(3):613-627 (May 1995).
Bell et al., "An Information-Maximization Approach to Blind Separation and Blind Deconvolution," Neural Computation, 7:1129-1159. (1995).
Haugland et al., "Cutaneous Whole Nerve Recordings Used for Correction of Footdrop in Hemiplegic Man," IEEE Transactions on Rehabilitation Engineering, 3(4):207-317 (Dec. 1995).
Afonso et al., "Comparing Stress ECG Enhancement Algorithms," IEEE Engineering in Medicine and Biology, pp. 37-44 (May/Jun. 1996).
Cardoso, "Infomax and Maximum Likelihood for Source Separation," IEEE Letters on Signal Processing, 4(4):112-114 (Apr. 1997).
Hilton, "Wavelet and Wavelet Packets Compression of Electrocardiogram," IEEE Transactions on Biomedical Engineering, 44(5):394-402 (May 1997).
Hyvärinen, "New Approximations of Differential Entropy for Independent Component Analysis and Projection Pursuit," In Advances in Neural Information Processing Systems, 10:273-279, MIT Press. (1997).
Sweldens, The lifting scheme: a construction of second generation wavelets. SIAM J. Math. Anal., 29(2):511-546 (Mar. 1998).
American National Standard ANSI/AAMI EC57:1998, Testing and Reporting Performance Results of Cardiac Rhythm and ST Segment Measurement Algorithms.

(56) References Cited

OTHER PUBLICATIONS

Tsalaile, et al. "Blind Source Extraction of Heart Sound Signals from Lung Sound Recordings Exploiting Periodicity of the Heart Sound," ICASSP 2008 IEEE, p. 461-464 (2008).

Torres-Pereira, et al. "A Biotelemetric Implantable Heart-Sound Rate Monitoring System," Proceedings of the XIV International Symposium on Biotelemetry, Apr. 6-11, 1997, Session 6-4, Marburg, German Abstract (1998).

Hyvärinen, "Fast and Robust Fixed-Point Algorithms for Independent Component Analysis," IEEE Transactions on Neural Networks, 10(3):626-634 (May 1999).

Cardoso, "High-Order Contrasts For Independent Component Analysis," Neural Comput., 11(1):157-192 (1999).

Chen et al., "Atomic Decomposition by Basis Pursuit," SIAM J. Scientific Computing, 20(1):33-61 (1999).

Pan et al., "Two Denoising Methods by Wavelet Transform," IEEE Trans. on SP, 47(12):3401-3406 (Dec. 1999).

Michaud et al., "Correlation waveform analysis to discriminate monomorphic ventricular tachycardia from sinus rhythm using stored electrograms from implantable defibrillators," PACE, 22(8):1146-1151 (Aug. 1999).

Mallat, "A Wavelet Tour of Signal Processing," 2nd Ed., 620 pgs., Academic Press, (Sep. 3, 1999).

Langley et al., "Comparison of three measures of QT dispersion," Conference: Computers in Cardiology, pp. 69-72 (Feb. 1999). (Abstract).

Goldberger et al., "PhysioBank, PhysioToolkit, and PhysioNet: Components of a New Research Resource for Complex Physiologic Signals," Circulation 101(23): e215-e220, Jun. 13, 2000).

Lu et al., "Wavelet Compression of ECG Signals by the Set Partitioning in Hierarchical Trees Algorithm," IEEE Transactions on Biomedical Engineering, 47(7):849-856 (Jul. 2000).

Marcellin et al., "An Overview of JPEG-2000," Proc. of IEEE Data Compression Conference, pp. 523-541 (2000).

Saul et al., "Periodic component analysis: an eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.

Taswell, "The What, How, and Why of Wavelet Shrinkage Denoising," Computing in Science and Engineering, vol. 2, No. 3, pp. 12-19 (2000).

Richman et al., "Physiological time-series analysis using approximate entropy and sample entropy", Am. J. Physiol. 278:H2039-H2049 (2000).

Sayood, "Introduction to Data Compression," 2nd ed., Academic Press, Morgan Kaufmann Publishers 2000.

Malik et al., "Measurement, interpretation and clinical potential of QT dispersion," J Am Coll Cardiol, 36(6):1749-1766 (Nov. 15, 2000).

Hyvärinen et al., "Independent Component Analysis: Algorithms and Applications," Neural Networks, 13(4-5):411-430 (2000).

Mayerburg, "Sudden Cardiac Death: Exploring the Limits of Our Knowledge," Journal of Cardiovascular Electrophysiology, 12(3):369-381 (Mar. 2001). (Abstract).

Brennan et al., "Do Existing Measures of Poincaré Plot Geometry Reflect Nonlinear Features of Heart Rate Variability?" IEEE Transactions on Biomedical Engineering, 48(11):1342-1347 (Nov. 2001).

Donoho et al., "Uncertainty Principles and Ideal Atomic Decomposition," IEEE Transactions on Information Theory, 47(7):2845-2862 (Nov. 2001).

Zibulevsky et al., "Blind Source Separation by Sparse Decomposition in a Signal Dictionary," Neural Computation. 13:863-882 (2001).

Oweiss et al., "MASSIT—Multiresolution Analysis of Signal Subspace Invariance Technique: a novel algorithm for blind source separation", Conference on Signals, Systems and Computers, 1:819-823 (2001).

M. Costa, A. L. Goldberger, and C.-K. Peng, Multiscale Entropy Analysis of Complex Physiologic Time Series, Phys. Rev. Lett. 89(6) (Aug. 5, 2002).

Kohler et al., "The principles of software QRS detection," IEEE Engineering in Medicine and Biology Magazine, 21(1):42-57 (2002).

\* cited by examiner

APNEIC/HYPOPNEIC ASSESSMENT VIA PHYSIOLOGICAL SIGNALS

OVERVIEW

Various aspects relate to processing of physiological signals for the detection and assessment of Apneic and/or Hypopneic events or Index (AHI), as may be applicable for patients undergoing evaluation or screen for sleep apnea.

It is estimated that about 22 million people in the U.S. suffer from Sleep Apnea (SA) with 80% of cases of moderate and severe sleep apnea going undiagnosed. A plethora of recent clinical evidence is finding and confirming that sleep disturbances such as sleep apnea impact a wide range of health issues including hypertension, atrial fibrillation (AF), stroke, depression, type 2 diabetes, and is a major contributor to traffic and heavy machinery accidents. About 84% of SA is obstructive sleep apnea (OSA). SA is most often diagnosed with a sleep study performed in either a clinic (Clinic Sleep Study—CSS) or at home (Home Sleep Test—HST). HST systems may include one or more of an SpO2 sensor, a nasal airflow sensor, and a chest band to measure respiration. HST has been rapidly gaining acceptance because it can be done at home. Further, HST may be more consistent than those obtained with CSS.

Various aspects of the present disclosure are directed to an apparatus, and as may be implemented in a related method, having communication circuitry for receiving data characterizing activity of a beating heart of a patient, communication circuitry for receiving data characterizing oxygen saturation measurements from the patient, and computing circuitry. The computing circuitry is configured and arranged to compute a time series of interbeat intervals from the data characterizing the activity of the beating heart, such as a recording thereof, and to decompose the time series into subcomponents. The computing circuitry is further configured and arranged to compute at least two emphasis signals based upon a selected subset of the subcomponents, each emphasis signal being computed using different formulas, and to choose the emphasis signal from the at least two emphasis signals based on coherence of the at least two emphasis signals with the oxygen saturation measurements. Using this approach, an emphasis signal that can be utilized to readily characterize oxygen saturation measurements may be identified and later used to detect further apneic/hypopneic events, which may be carried out without using oxygen saturation measurements.

Another embodiment is directed to a method carried out as follows. An hypopneic and/or apneic event (AHE) is detected based upon an oxygen saturation signal, and a time series of interbeat intervals obtained during the AHE event are computed. The time series is decomposed into subcomponents and a subset of the subcomponents, which has central frequencies corresponding to a range of frequencies exhibited during periodic breathing in apnea-hypopnea events, is selected. Emphasis signals are computed based upon, for each emphasis signal, at least one respective subcomponent in the subset. One of the emphasis signals is selected based upon coherence between the emphasis signals and the oxygen saturation signal, and the selected emphasis signal is used to detect further AHEs. In some implementations, the selected emphasis signal is used to detect further AHEs independently from oxygen saturation signals, therein facilitating detection of the AHEs without using pulse oximetry.

Another embodiment is directed to an apparatus for detecting an (AHE) in a patient, which includes communication circuitry for receiving data characterizing activity of a beating heart of a patient and data characterizing oxygen saturation measurements from the patient, as well as computing circuitry to identify the presence of the AHE based upon oxygen saturation measurements. The computing circuitry carries out a self-learning function by computing an emphasis signal for the patient based upon beat-to-beat heart rate measurements and oxygen saturation measurements obtained while an AHE is present. After computing the emphasis signal, the computing circuitry detects further AHEs using the computed emphasis signal independently from oxygen saturation measurements from the patient.

Another embodiment is directed to a method as follows. A time series of interbeat intervals are computed from a recording of activity of a beating heart, the time series is decomposed into subcomponents, and the frequency and amplitude of oscillation of the subcomponents is determined. Subcomponents that identify an event related to sleep apnea are detected based upon amplitude and frequency characteristics of the subcomponents corresponding to cyclic variation of interbeat intervals exhibited in sleep apnea.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims.

DESCRIPTION OF THE FIGURES

Various example embodiments may be more completely understood in consideration of the following detailed description in connection with the accompanying drawings, in which.

Figure 1A:
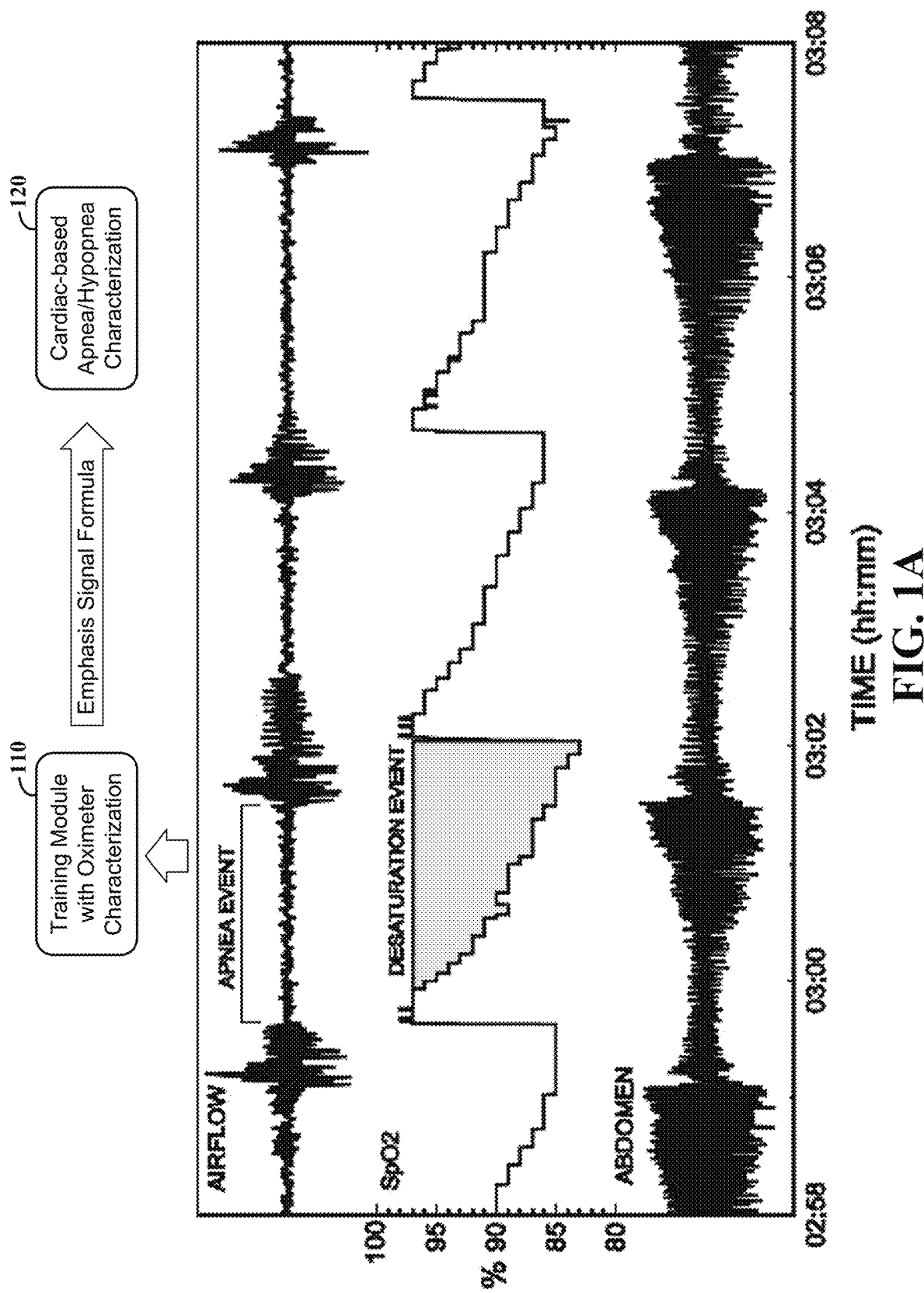
FIGS. 1A and 1B show an apparatus and related signals as may be implemented for characterizing apneic and or hypopneic events, in accordance with one or more embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Various example embodiments characterized herein relate to the processing of physiological signals for detecting AHEs. Such an approach can be utilized to assess AHI for diagnosing and screening sleep apnea. Such approaches can facilitate screening of patients for sleep apnea in an easy to use, inexpensive, non-invasive, and accurate test. Further, such embodiments may realize a diagnostic performance benefit in the repeated measures available from HST. While the present invention is not necessarily limited to such applications, various aspects of the invention may be appreciated through discussion of examples used in his context.

Various aspects of the present disclosure are directed to apparatuses and/or methods involving the generation and identification of an emphasis signal, and related formula, for utilizing cardiac signals for detecting apneic and/or hypopneic events. In a particular embodiment, communication circuitry is utilized for receiving data characterizing activity of a beating heart and data characterizing oxygen saturation measurements from a patient. Computing (e.g., logic) circuitry computes a time series of interbeat intervals from the data characterizing the activity of the beating heart, such as from a recording thereof, and decomposes the time series into subcomponents. Emphasis signals are computed based upon a selected subset of the subcomponents, each emphasis signal being computed using different formulas, and one of the emphasis signals is selected based on coherence of the emphasis signals with the oxygen saturation measurements. The different formulas may, for example, include a common set of formulae with different weights applied to respective components. The selected emphasis signal may then be utilized to readily characterize oxygen saturation measurements (e.g., desaturation events) and/or otherwise characterize apneic/hypopneic events from further cardiac signals, which may achieved without using oxygen saturation measurements.

In some instances, further apnea-hypopnea events may be detected by decomposing a further time series of interbeat intervals from further data characterizing the activity of the beating heart. A further emphasis signal is calculated from the further time series, based on the formula for computing the chosen emphasis signal (e.g., with particular functions and/or weighting). Apnea-hypopnea events are detected based on amplitude and frequency characteristics of the further emphasis signal, for example as compared to amplitude and frequency characteristics of the selected emphasis signal during a known apneic/hypopneic event. In some implementations, the computing circuitry detects the apnea-hypopnea events by computing an envelope of the further emphasis signal, computing an amplitude of the envelope and a frequency of oscillation of the further emphasis signal by measuring zero crossings of the emphasis signal. Apnea-hypopnea events may then be detected by computing a coefficient of cyclic variation of the emphasis signal.

The computing circuitry may select the subset of ones of the subcomponents in a variety of manners. In some embodiments, subcomponents that pertain to a respiratory component of the activity of the beating heart are selected, for example by using known components (e.g., frequencies) relevant to respiratory functions. The computing circuitry may select the subset of the subcomponents as subcomponents of a portion of the time series that pertain to a component of the activity of the beating heart that is responsive to a sleep apnea event.

In a more particular implementation, the computing circuitry selects the subset of the subcomponents by identifying ones of the subcomponents from a frequency range of the data characterizing the beating heart that correspond to respiratory components, and select the subset of the subcomponents from the identified subcomponents in response to an apnea-hypopnea event. In some implementations, the computing circuitry selects the subset of the subcomponents from the identified subcomponents by correlating timing characteristics of the subcomponents with timing characteristics of a pulse oximetry signal indicating the apnea-hypopnea event. In certain implementations, the computing circuitry chooses the emphasis signal from the at least two emphasis signals based on coherence of the at least two emphasis signals with oxygen saturation measurements from the patient during the apnea-hypopnea event.

Another embodiment is directed to an apparatus for detecting apnea-hypopnea events, utilizing communication circuitry for receiving data characterizing activity of a beating heart of a patient and data characterizing oxygen saturation measurements from the patient, as well as computing circuitry that detects apnea-hypopnea events. The computing circuitry calculates a time series of interbeat intervals from the data characterizing the activity of a beating heart, decomposes the time series into subcomponents, and selects a subset of the subcomponents with central frequencies corresponding to a range of frequencies exhibited during periodic breathing in apnea-hypopnea events as indicated by the oxygen saturation measurements. One or more of the subcomponents is/are selected from the subset based upon characteristics of the patient's periodic breathing during apnea-hypopnea events. Apnea-hypopnea events are detected in further data characterizing the activity of the beating heart, based upon amplitude and frequency characteristics of the at least one subcomponent.

The computing circuitry may select the one or more subcomponents in a variety of manners. In some embodiments, emphasis signals obtained during an apnea-hypopnea event are computed, and coherence between the emphasis signals and an oxygen saturation signal is determined. An emphasis signal is selected from the computed emphasis signals based on coherence between the computed emphasis signals and the oxygen saturation signal, and one or more subcomponent is selected from subcomponents of the emphasis signal. Apnea-hypopnea events may be detected in further data characterizing the activity of the beating heart by decomposing a time series of the further data into subcomponents and selecting at least one further subcomponent therefrom, using a formula used to select said at least one subcomponent in the subset. The apnea-hypopnea events can be detected based upon a comparison of amplitude and frequency characteristics of the further subcomponent with amplitude and frequency characteristics of said at least one subcomponent.

In accordance with another example embodiment, an apparatus for detection of apnea-hypopnea events includes circuitry for receiving physiological signal data, and logic circuitry to characterize apnea-hypopnea events as follows. A time series of interbeat intervals is computed from aspects of the physiological signal data characterizing activity of a beating heart of a patient, and the time series is decomposed into subcomponents. Subcomponents having characteristics that correlate most closely to, relative to the other subcomponents, characteristics of oxygen saturation during an oxygen desaturation event in the patient are identified. An event related to sleep apnea is detected from another time series of interbeat intervals computed from further aspects of the physiological signal data, based upon the characteristics of the identified subcomponents.

In some implementations, the logic circuitry measures or receives oxygen saturation via a sensor, and detects the oxygen desaturation events by comparing blood oxygen level to a threshold. The blood oxygen level is used to ascertain characteristics of the subcomponents corresponding to cyclic variation of interbeat intervals exhibited during sleep apnea in a patient. These ascertained characteristics may include amplitude characteristics, frequency characteristics, or a combination of amplitude and frequency characteristics. The logic circuitry may further maintain detection accuracy in the absence of blood oxygen measurements once the ascertained characteristics have been obtained, and may generate an output indicative of the detected event.

Figure 1B:
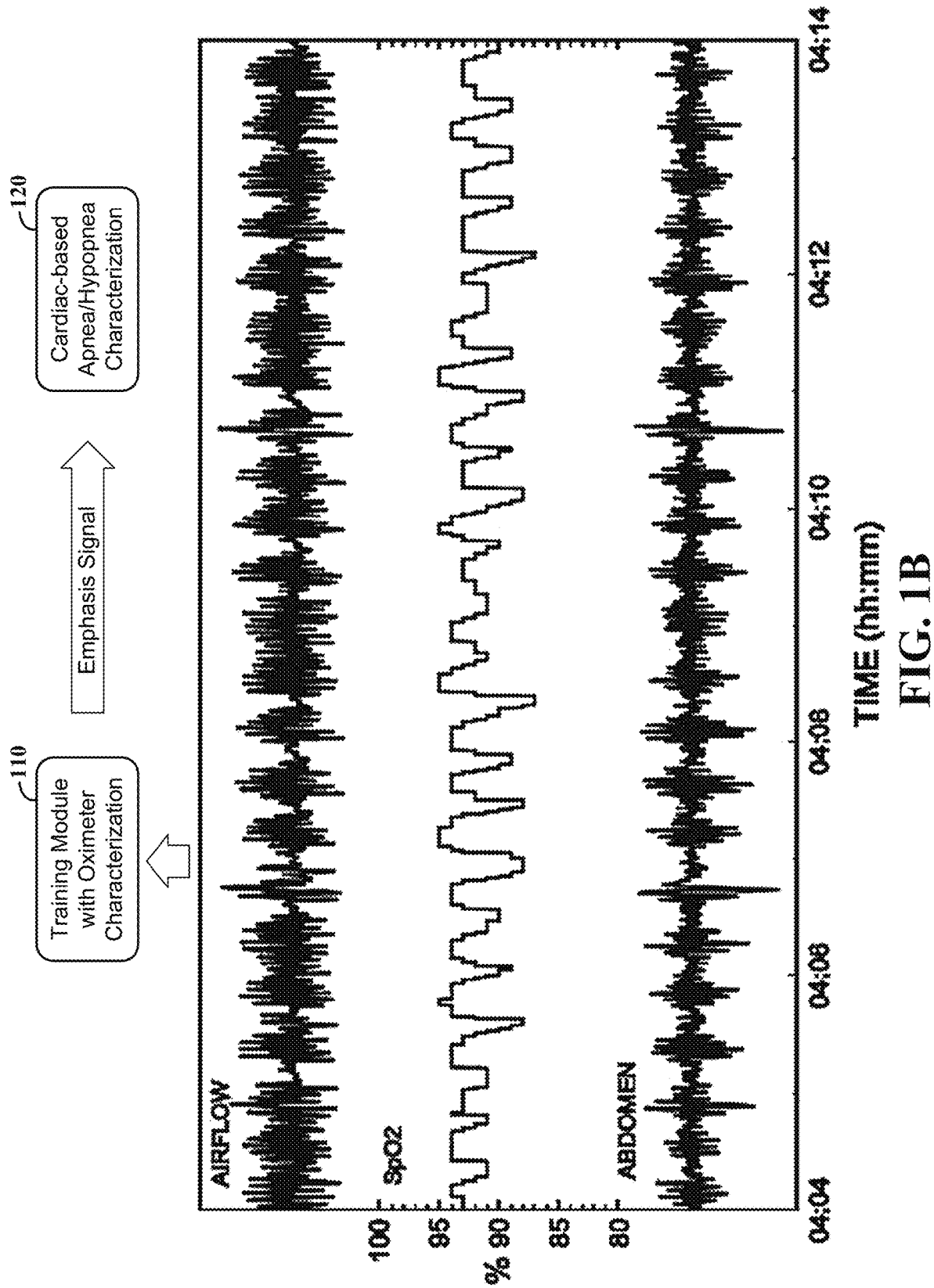

FIGS. 1A and 1B show airflow, SpO2, and respiratory effort in two patients with equally severe sleep apnea (from Turkish Arch. of Otolaryngology), along with a training module 110 having an oximeter characterization, and a cardiac-based apnea/hypopnea characterization module 120, as may be assessed in accordance with one or more embodiments. During an apnea event, airflow and SpO2 drops, and respiratory effort (labeled abdomen in FIG. 1) increases. Both of these patients may be diagnosed with severe sleep apnea, but the character of the oxygen desaturation, respiratory effort, and airflow are quite different. The cyclic alternating patterns in the patient represented in FIG. 1A shows episodes occurring at 2.5 minute intervals while the cyclic alternating pattern in the patient represented in FIG. 1B shows episodes occurring every 12 seconds. This demonstrates that the characteristics of equally severe episodes can vary significantly. The training module 110 operates to characterize an emphasis signal for cardiac function that characterizes an apneic or hypopneic event, based on oximeter characterization.

The emphasis signal is used, based on a formula used to calculate the emphasis signal, by the cardiac-based apnea/hypopnea characterization module 120 to identify apneic and/or hypopneic events. This latter characterization may be utilized independent from any further oximetry, by using the trained signal/formula. In this context, once trained, the cardiac-based apnea/hypopnea characterization module 120 can be used to detect apneic/hypopneic events in the respective patients characterized by the signals in FIGS. 1A and 1B without further need for oximetry. This approach may be particularly useful, for example, in assessing such events in respective patients without needing to utilize an oximeter sensor, which can address problems relating to patient comfort and others as noted in the Overview section above.

Many embodiments described here broadly reference use of an approach involving the decomposition of cardiac signals into subcomponents, computation of emphasis signals based on selected subsets of the subcomponents, and selection of one of the emphasis signals that facilitates identification of an apneic/hypopneic event. In connection with one or more embodiments, it has been recognized/ discovered that such decomposition and related subset selection can be particularly useful for identifying subcomponents that characterize apneic/hypopneic events, with high accuracy. Training such an approach using oximeter-based detection of apneic/hypopneic events (or other such detection) and generation of a formula used for calculating an emphasis signal can be used to identify such an emphasis signal/formula that accurately identifies such an event for a particular patient. Once identified, the formula can be used to detect, with the same patient, apneic/hypopneic events based on cardiac function and, if desired, without oximeter-based detection. In various embodiments, this approach involves using Multi-Domain Signal Processing (MDSP), which is an approach to signal processing applicable to pseudoperiodic physiologic signals and can be used for removing in-band noise. In some embodiments MDSP includes the use of wavelet decomposition to decompose a physiologic signal into subcomponents. Various such embodiments, or other signal processing embodiments, may be implemented in accordance with one or more of the following U.S. Pat. Nos. 8,632,465; 9,294,074; 8,478,389; 9,339,202; 10,028,706; 8,543,195; 9,414,786; 9,408,549; 9,492,096; 9,314,181; 9,713,431; and 9,706,956, all of which are incorporated herein by reference.

Figure 2:
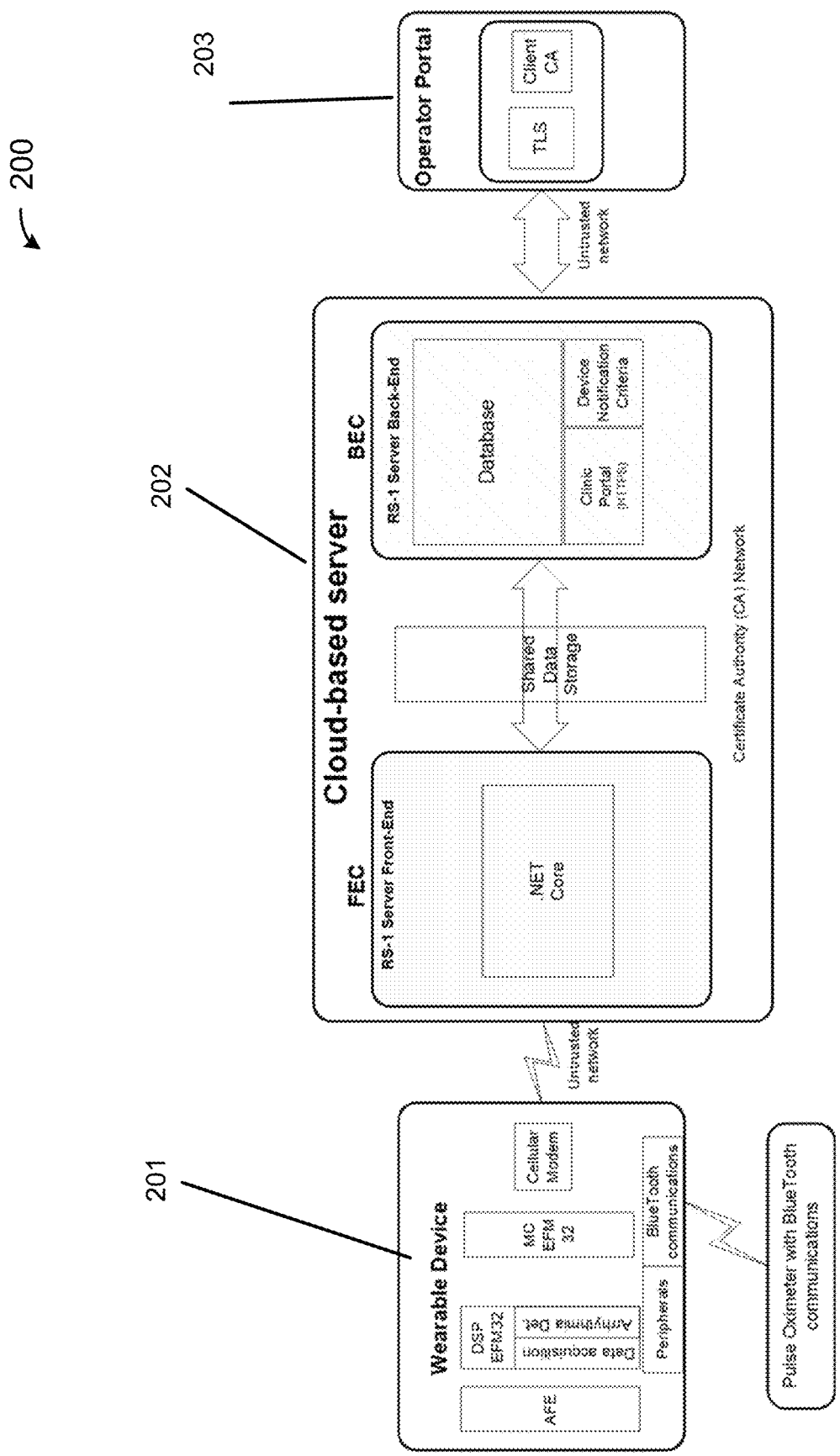
FIG. 2 shows an apparatus for characterizing apneic and or hypopneic events, as may be implemented in accordance with one or more embodiments.

Various embodiments are directed to use of the Remote Cardiac Monitoring System (RCMS) 200 of FIG. 2. The system shown in FIG. 2 may be implemented for patients who have or are at risk of having cardiac disease and those that demonstrate intermittent symptoms indicative of cardiac disease and require cardiac monitoring on a continuing basis monitoring of arrhythmias, and may utilize the RX-1 cardiac monitoring apparatus available from VivaQuant of Shoreview, Minnesota.

In one embodiment, the RCMS 200 includes wearable device 201 that captures patient ECG, processes the ECG to remove noise, may identify arrhythmias, and communicates data to a server 202, represented by way of example as a cloud-based server. Wearable device 201 is shown as including various blocks/circuits by way of example, and may employ MDSP signal processing to remove noise and extract diagnostic information from the acquired ECG. In one embodiment, RCMS 200 provides for automatic real-time ECG acquisition and arrhythmia detection. The server 202 may communicate findings and data to Operator Portal (OP) 203, which may provide visualization tools and report generation functions to provide for summarization of clinically actionable information in a report provided to a physician to aid in diagnosis.

In certain embodiments, the RCMS 200 operates as follows. The wearable device 201 collects cardiac and oxygen saturation data from a patient. The server 202 includes communication circuitry for receiving data characterizing activity of a beating heart of the patient, and communication circuitry for receiving data characterizing oxygen saturation measurements from the patient. The aforementioned communication circuitry may be implemented in a common communication circuit using common components. The server 202 further includes computing circuitry configured and arranged to compute a time series of interbeat intervals from the received data characterizing the activity of the beating heart. The computing circuitry is further configured to decompose the time series into subcomponents, and compute, using different formulas, at least two emphasis signals based upon a selected subset of the subcomponents. The computing circuitry is also configured to choose an emphasis signal from the at least two emphasis signals based on coherence of the at least two emphasis signals with the oxygen saturation measurements. In this context, the chosen emphasis signal may be useful for characterizing cardiac-based function that correlates to oxygen saturation measurements, which relate to an apneic and/or hypopneic event. Such an event may thus be detected using cardiac-based function, independent from (e.g., without using) oxygen saturation measurements. Once an emphasis signal is chosen (e.g., during a self-learning cycle utilizing an oximeter), this chosen signal may be used to facilitate assessment of conditions such as sleep apnea without using an oximeter, which can facilitate patient comfort.

Figure 3:
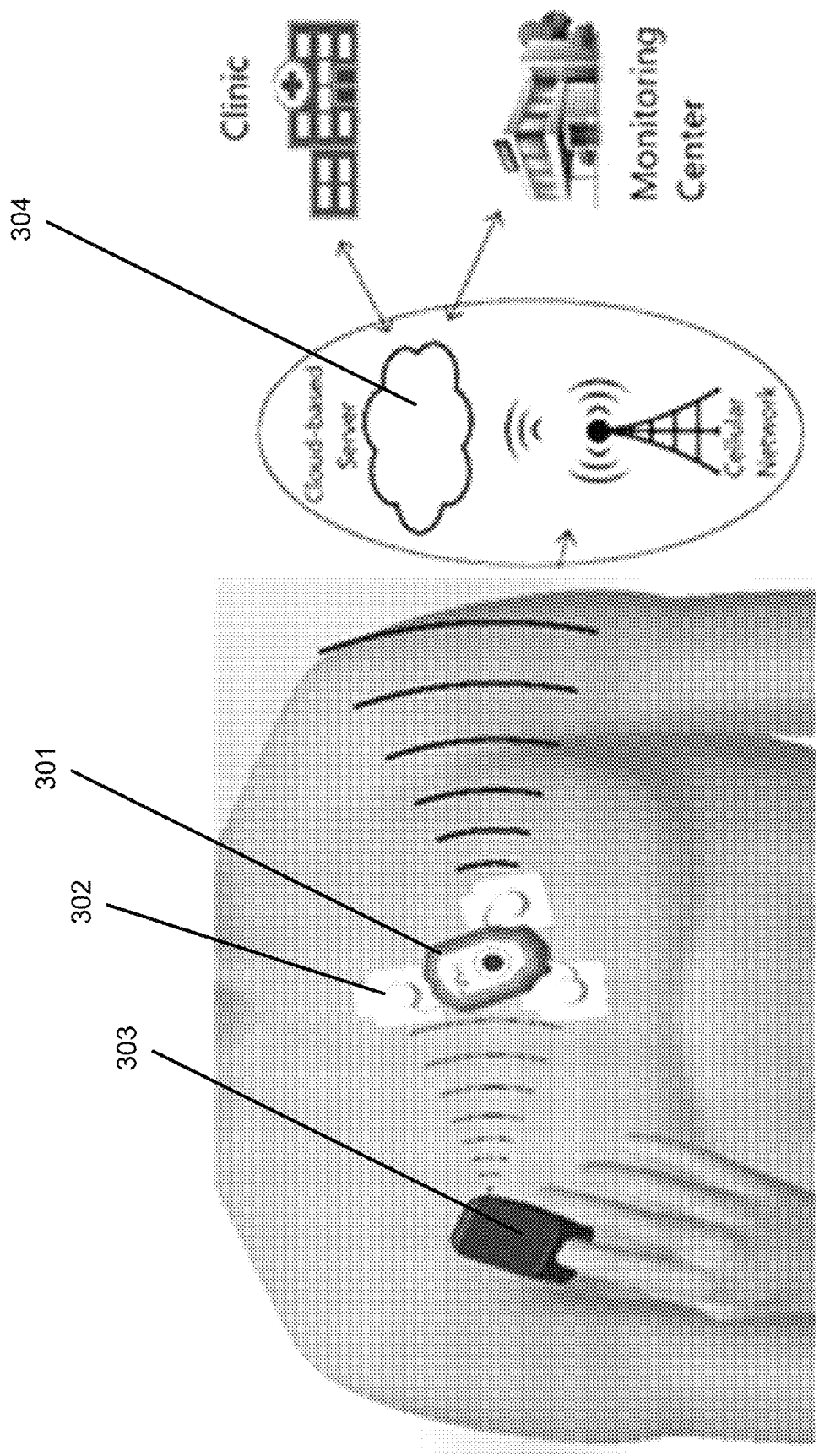
FIG. 3 shows a system for characterizing apneic and or hypopneic events, as may be implemented in accordance with one or more embodiments.

Referring to FIG. 3, wearable device 301 collects ECG, movement activity, and SpO2, as may be implemented in accordance with one or more example embodiments. In one embodiment, an ECG is sensed by electrodes 302 and movement activity is sensed by an accelerometer located within wearable device 301. In one embodiment, SpO2 sensor 303 and wearable device 301 include wireless communication capabilities such as Bluetooth low-energy (BTLE) that enables wearable device 301 circuitry to receive SpO2 measurements from SpO2 sensor 303.

In certain embodiments, wearable device 301 receives information wirelessly from other types of sensors, both wearable and non-wearable. For instance, the collection of additional information may extend capabilities of the RCMS beyond sleep apnea, such as to management of chronic diseases that may include, for example, heart failure. These sensors may include blood pressure, body weight, impedance, temperature, glucose, pCO2, respiratory bands (for measuring movement of the chest and abdominal wall), and other sensors. Wearable device 301 communicates with server 304 (e.g., cloud-based) which may provide access to extracted diagnostic information and raw data. In some embodiments, diagnostic information is extracted by wearable device 301, while in other embodiments it is extracted by the server from data communicated from wearable device 301. In yet other embodiments, wearable device 301 extracts intermediate information from the raw patient data (e.g., ECG, SpO2, activity) and the remainder of the processing is performance on the server Processing data on wearable device 301 may be beneficial to system performance by reducing the amount of data required to be communicated to the server, which may also reduce power requirements. Further, processing data on wearable device 301 enables "point of care" information delivered directly to the patient or as feedback to a therapy device, even in the absence of cellular connectivity. Processing data on server 304 may be beneficial because the additional computational power available enables the use of more sophisticated analytics that can potentially improve accuracy of extracted diagnostic information.

In one embodiment which may be useful for diagnosing sleep apnea and hypopnea, a time series of inter-beat intervals is computed from an ECG recording, as may be obtained for example via wearable device 201 and/or 302, and used to detect the presence of sleep apnea or hypopnea. In one embodiment, an interbeat interval sequence is resampled to create an equispaced series and is then decomposed into subcomponents. A subset of these subcomponents is selected to compute an emphasis signal based upon a priori knowledge of the frequency of cyclic patterns present in patients with sleep apnea. In one embodiment, the emphasis signal is computed from a subset of the subset of subcomponents. To detect apneic and hypopneic events (AHE), amplitude and frequency of oscillation of the emphasis signal is quantified. In one embodiment, amplitude is quantified by computing an envelope based upon the peak values of the emphasis signal. In another embodiment, frequency is quantified by assessing zero crossing of an envelope computed based upon peak values of each subcomponent. In another embodiment the amplitude and frequency are quantified by computing a coefficient of cyclic variation, such as characterized in A. Fulford, 2014. Cyclic variation may be identified in a manner similar to identifying amplitude and frequency of a best fitting sine wave. When the frequency of the emphasis signal corresponds to cyclic patterns associated with AHE and the amplitude exceeds a predefined threshold, AHE may be detected.

In an alternate embodiment, SpO2 measurements may be employed in conjunction with ECG measurements to improve the detection accuracy of AHE. This approach may be carried out using the apparatus shown in FIG. 3, with SpO2 sensor 303 in wireless communication with wearable device 301. The wearable device processes SpO2, ECG, and activity to detect AHE. AHE and arrhythmias are communicated to a monitoring center, such as via the cellular network.

In another embodiment, SpO2 is measured to detect AHE. An AHE event is detected when SpO2 falls below a predetermined threshold. SpO2 is used a direct measure of apneic episodes and may facilitate accurate detection of AHE. ECG is a direct measure of autonomic response to cessation of airflow and may facilitate accurate detection of AHE. Correlation between SpO2 measurements and ECG measurements may be utilized to train a model for detecting AHE in a particular patient, using that patient's ECG.

Figure 4:
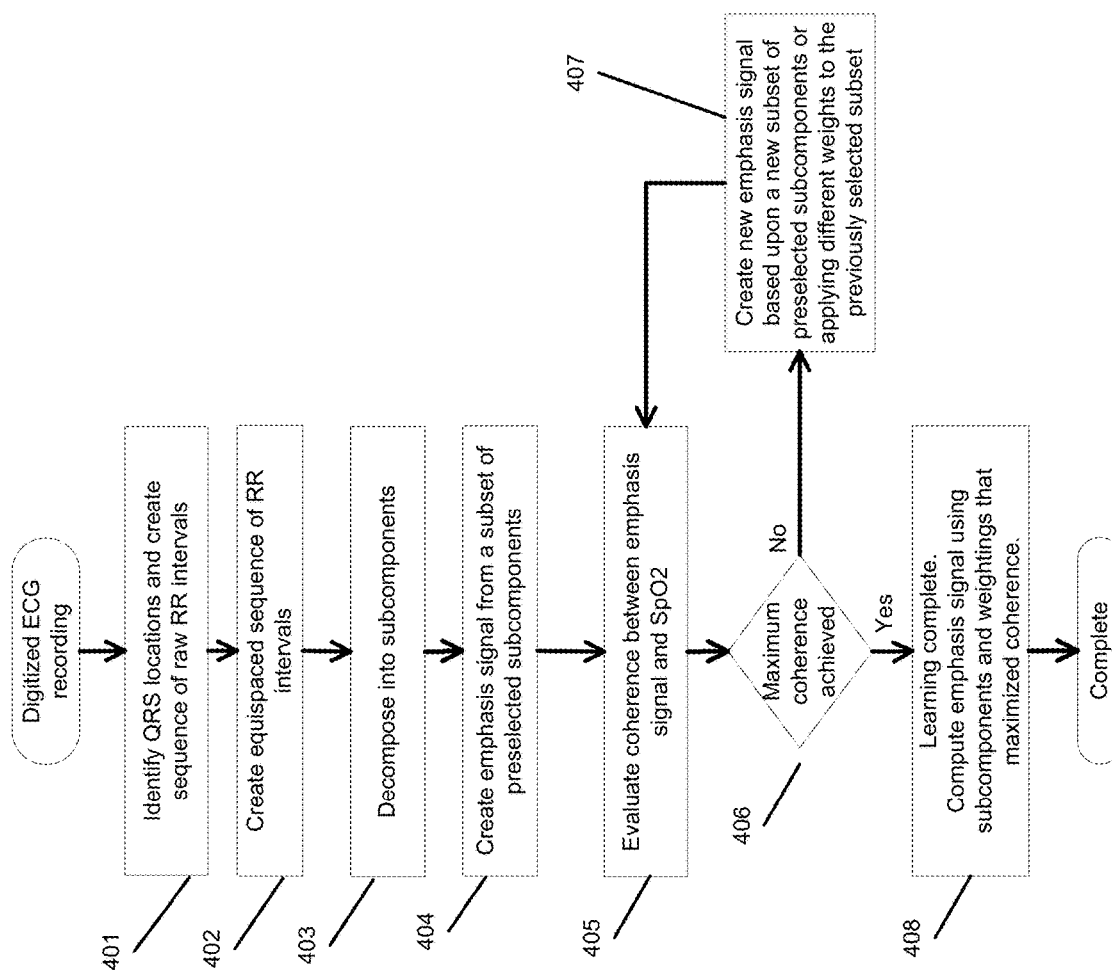
FIG. 4 shows a data flow diagram for characterizing apneic and or hypopneic events, as may be implemented in accordance with one or more embodiments.

FIG. 4 shows a self-learning approach for identifying an emphasis signal, which may be carried out on a patient-by-patient basis, which provides an accurate indication of an AHE event for a patient. At block 401, a digitized ECH recording is processed to identify QRS locations and create a sequence of RR intervals, which are further processed at block 402 to create an equispaced sequence of the intervals. These (e.g., beat-to-beat) intervals are decomposed into subcomponents at block 403, and an emphasis signal is computed from a subset of the subcomponents at block 404. Coherence between the emphasis signal sand oxygen data (SpO2) is evaluated at block 405, and if a maximum or near maximum coherence is achieved at block 406, learning is complete and the emphasis signal is computed using subcomponents and weightings that maximize coherence. If the emphasis signal is not in desired coherence at block 406, a new emphasis signal is created at block 407, based on a new subset of subcomponents and/or applying different weights to the subcomponents used at block 404.

Figure 5:
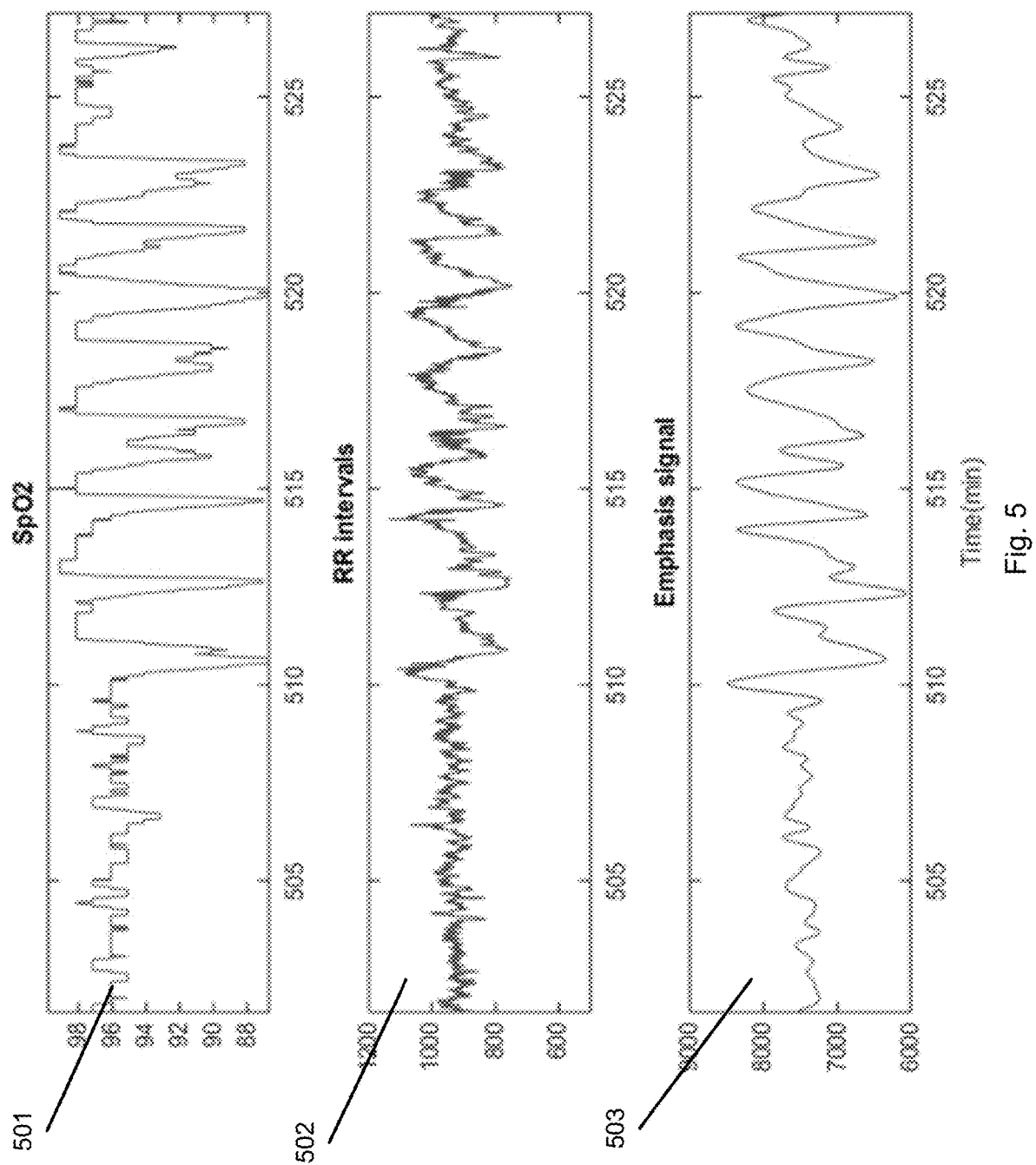
FIG. 5 shows a plots of respective signals implemented for characterizing apneic and or hypopneic events, as may be implemented in accordance with one or more embodiments.

FIG. 5 shows concurrent SpO2 501, RR interval trend 502, and emphasis signal 503 during periodic desaturations caused by hypopnea, as may be computed in connection with one or more embodiments herein. Note that the cyclic variability in an emphasis signal, such as in an ideal emphasis signal, may closely correspond to periodic desaturations in the SpO2 signal.

Referring to FIGS. 4 and 5, signals may be processed and generated as follows, in accordance with an embodiment. ECG data may be processed to remove in-band noise using MDSP signal processing, QRS complexes in the ECG may be detected, and a sequence of beat-to-beat RR intervals may be completed, at block 401. The resulting RR intervals may be interpolated and resampled to create 4 Hz equispaced RR interval at block 402, depicted in trend 502. In one embodiment, the resulting RR trend is post-processed by decomposing the RR intervals into subcomponents at block 403. A subset of preselected components corresponding to the periodic breathing range are combined to produce a wavelet-generated emphasis signal 503, at block 404, that enhances response to signal variations in the frequency range of periodic breathing. In one example, the frequency range of periodic breathing ranges from 0.01 to 0.3 Hz. In one embodiment, the SpO2 signal is used as a tool to improve the accuracy of AHE detection using only ECG-derived measurements. Once the emphasis signal has been optimized by maximizing (or about maximizing) coherence with SpO2 during AHE events, the SpO2 signal may no longer provide improvements in detection accuracy. This may have the benefit of allowing the patient to no longer wear the SpO2 sensor and proceed with the remainder of the test more comfortably.

As utilized herein, the term maximizing as pertaining to an emphasis signal may refer to choosing a signal that meets a desired threshold, which exhibits a best match relative to other signals, or a combination thereof. As such, such a signal may not necessarily exhibit a maximum-attainable coherence, but rather a desirable coherence relative to available signals. In some implementations, frequency and amplitude fluctuations of emphasis signals are approximated, such as by using a least squares fit of a sine function to each emphasis signal, and then choosing one of the emphasis signals based on a best or desirable least squares fit.

The emphasis signal 503 may be computed by combining a subset of the preselected subcomponents. In one embodiment the subcomponents are combined as a weighted average. In one embodiment, the subset is determined by adaptive selection to enhance the coupling between SpO2 and the resulting emphasis signal. Other embodiments utilize a combination of a weighted average and adaptive selection. Adaptive selection may be accomplished by computing an emphasis signal (as at block 404), evaluating coherence (as at block 405), testing for a maxima (as at block 406), computing another emphasis signal (as at block 407), and continuing until a local maxima is achieved. Once the subcomponents and weightings that provide a maxima are identified they may be used to process the beat-to-beat heart rate data for that patient going forward (as at block 408). Once found, the use of SpO2 may no longer provide an improvement in accuracy of AHE detection.

In one embodiment the periodicity of emphasis signal 503 may be quantified using nonlinear dynamic analysis and compared to the periodicity of SpO2, such as may be carried out at block 405 in FIG. 4. The comparison may be accomplished by evaluating the coupling between the periodic variability of SpO2 and the emphasis signal. In another embodiment, coupling is quantified as a product of coherence and cross spectral power. In yet another embodiment, the amplitude and phase of SpO2 and the emphasis signal are each computed and compared.

In one embodiment, target subcomponents used to compute the emphasis signal are adaptively selected from the set of preselected subcomponents to maximize coupling between SpO2 501 and emphasis signal 503. It has been recognized/discovered that adaptation may be useful because the cyclic variation of heart rate is driven by a reflex, which changes character as the progression of sleep apnea becomes more blunted, typically over the course of months to years. It has been further recognized/discovered that the ability of the detection algorithm to adapt the computational aspects of the emphasis signal to maximize coupling with the SpO2 signal may be advantageous to improving the algorithm's ability to accurately detect AHE from heart rate measurements.

In yet another embodiment, motor activity and posture are measured. Arousal during an AHE event may result in patient movement that can be sensed using an accelerometer. In one embodiment the accelerometer is located within wearable device 301 in FIG. 3. The presence of arousal can be used to qualify diagnosis obtained from RR interval measurements. For example, if activity is observed during sleep then it is more likely that the patient is aroused and may disqualify an AHE detection. In one embodiment, the detection algorithm will only be activated once measurements from the accelerometer indicate the patient is supine with low activity levels. In addition, patients that suffer from restless leg syndrome may have heart rate fluctuations that often correlate with leg movements and the heart rate oscillations are similar in frequency in frequency to the heart rate oscillations induced by apnea. In one embodiment, in patients with restless leg syndrome, an accelerometer is used to detect leg movements with such detection used to reduce the rate of false positive AHE.

In another embodiment, the algorithm may not employ the SpO2 sensor at all times while ECG is monitored on the patient. This may occur because a patient does not want to wear the SpO2 sensor all the times because it is uncomfortable, the sensor may fall off, or it may come loose and not provide accurate measurements.

In one embodiment, during the time an SpO2 sensor is providing accurate measurements, episodes detected by the SpO2 sensor are used as a training set by the ECG-based algorithm to identify the individual cycling frequency of heart rate corresponding to AHE. This may be useful for improving the accuracy of event detection based upon ECG, as the individual cycling frequency of heart rate in response to airflow obstruction may vary from patient to patient and over the course of time within a patient as disease progresses. In one embodiment information from the SpO2 sensor is used to detect the presence of AHE. Similarly, other parameters of the ECG-based algorithm, such as QT interval, can be used to assess other cardiovascular risk associated with AHE and monitor the impact of therapy for these patients.

In one embodiment, an algorithm as characterized herein is trained in a semi-supervised fashion, enabling it to incorporate additional labels, such as SpO2 when available. This approach, using information from the SpO2 sensor, to learning will allow it to compensate the ECG-based algorithm for inter-subject variability in factors that mediate HR response to AHE, such as autonomic tone, cardiopulmonary interaction and comorbidities. Hence, accuracy of the ECG-based algorithm can be improved using the SpO2 sensor, providing improved detection accuracy even when the patient is not wearing the SpO2 sensor.

The accuracy of the ECG-based algorithm may utilize the accuracy of a QRS detector as characterized herein. This approach may be used in an ambulatory setting, and ambulatory ECGs are often corrupted with noise. In one embodiment, the ECG is denoised to improve R-wave peak detection accuracy.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., obtaining a signal, denoising a signal, computing an emphasis signal, maximizing, or generating an output indicative of a physiological characteristic). For example, in certain of the above-discussed embodiments, one or more modules are discrete logic circuits or programmable logic circuits configured and arranged for implementing these operations/activities, as in the circuit modules shown in FIGS. 1A, 1B, 2 and 3. Such modules or blocks may be implemented at a remote location such as in a server, clinic or monitoring center, and/or in local wearable device. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules may include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform operations/activities as characterized herein.

Based upon the above discussion and illustrations, various modifications and changes may be made to embodiments and implementations characterized herein, without strictly following such exemplary embodiments and applications. For example, applications related to apneic/hypopneic detection can be implemented in other scenarios, as noted herein. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
   communication circuitry for receiving data characterizing activity of a beating heart of a patient;
   communication circuitry for receiving data characterizing oxygen saturation measurements from the patient; and
   computing circuitry configured and arranged to:
   compute a time series of interbeat intervals from the data characterizing the activity of the beating heart;
   decompose the time series into subcomponents;
   compute at least two emphasis signals based upon a selected subset of the subcomponents, each emphasis signal being computed using different formulas; and
   choose an emphasis signal from the at least two emphasis signals based on coherence of the at least two emphasis signals with the oxygen saturation measurements.

2. The apparatus of claim 1, wherein the computing circuitry is configured and arranged to detect an apnea-hypopnea event by:
   decomposing a further time series of interbeat intervals from further data characterizing the activity of the beating heart;
   computing a further emphasis signal from the further time series based on the formula for computing the chosen emphasis signal; and
   detecting the apnea-hypopnea event based on amplitude and frequency characteristics of the further emphasis signal.

3. The apparatus of claim 2, wherein the computing circuitry is configured and arranged to detect the apnea-hypopnea event based on the amplitude and frequency characteristics of the further emphasis signal by:
   computing an envelope of the further emphasis signal;
   computing an amplitude of the envelope of the further emphasis signal; and
   computing a frequency of oscillation of the further emphasis signal by measuring zero crossings of the further emphasis signal.

4. The apparatus of claim 3, wherein the computing circuitry is configured and arranged to detect the apnea-hypopnea event by computing a coefficient of cyclic variation of the emphasis signal.

5. The apparatus of claim 1, wherein the computing circuitry is configured and arranged to select the subset of the subcomponents that pertain to a respiratory component of the activity of the beating heart.

6. The apparatus of claim 1, wherein the computing circuitry is configured and arranged to select the subset of the subcomponents as subcomponents of a portion of the time series that pertain to a component of the activity of the beating heart that is responsive to a sleep apnea event.

7. The apparatus of claim 1, wherein the computing circuitry is configured and arranged to select the subset of the subcomponents by:
   identifying ones of the subcomponents from a frequency range of the data characterizing the activity of the beating heart that correspond to respiratory components; and
   select the subset of the subcomponents from the identified ones of the subcomponents in response to an apnea-hypopnea event.

8. The apparatus of claim 7, wherein the computing circuitry is configured and arranged to select the subset of the subcomponents from the identified ones of the subcomponents by correlating timing characteristics of the subcomponents with timing characteristics of a pulse oximetry signal indicating the apnea-hypopnea event.

9. The apparatus of claim 7, wherein the computing circuitry is configured and arranged to choose the emphasis signal from the at least two emphasis signals based on the coherence of the at least two emphasis signals with the oxygen saturation measurements by using the at least two emphasis signals computed based on the selected subset of the subcomponents obtained from the patient during the apnea-hypopnea event.

10. An apparatus for detecting apnea-hypopnea events, the apparatus comprising:
    communication circuitry for receiving data characterizing activity of a beating heart of a patient;
    communication circuitry for receiving data characterizing oxygen saturation measurements from the patient; and
    computing circuitry configured and arranged to:
    compute a time series of interbeat intervals from the data characterizing the activity of the beating heart;
    decompose the time series into subcomponents and select a subset of the subcomponents with central frequencies corresponding to a range of frequencies exhibited during periodic breathing in the apnea-hypopnea events as indicated by the data characterizing the oxygen saturation measurements;
    select at least one subcomponent in the subset based upon characteristics of the patient's periodic breathing during the apnea-hypopnea events, by
    computing emphasis signals obtained during one of the apnea-hypopnea events;
    evaluating coherence between the computed emphasis signals and the data characterizing the oxygen saturation measurements from the patient; and
    selecting an emphasis signal from the computed emphasis signals based on coherence between the computed emphasis signals and the data characterizing the oxygen saturation measurements from the patient, and selecting the at least one subcomponent from subcomponents of the selected emphasis signal; and
    detect the apnea-hypopnea events in further data characterizing the activity of the beating heart, based upon amplitude and frequency characteristics of the at least one subcomponent.

11. The apparatus of claim 10, wherein the computing circuitry is configured and arranged to detect the apnea-hypopnea events in the further data characterizing the activity of the beating heart by:
    decomposing a time series of the further data into subcomponents and selecting at least one further subcomponent therefrom using a formula used to select said at least one subcomponent in the subset; and detecting the apnea-hypopnea events based upon a comparison of amplitude and frequency characteristics of the further subcomponent with the amplitude and frequency characteristics of said at least one subcomponent.

12. A method comprising:

detecting a presence of an apnea-hypopnea event (AHE) based upon an oxygen saturation signal;

computing a time series of interbeat intervals obtained during the AHE;

decomposing the time series into subcomponents and selecting a subset of the subcomponents with central frequencies corresponding to a range of frequencies exhibited during periodic breathing in apnea-hypopnea events;

computing emphasis signals based upon, for each emphasis signal, at least one respective subcomponent in the subset;

selecting one of the emphasis signals based upon coherence between the emphasis signals and the oxygen saturation signal; and using the selected one of the emphasis signals to detect further AHEs.

13. The method of claim 12, wherein using the selected one of the emphasis signals to detect the further AHEs includes detecting the further AHEs independently from oxygen saturation signals, therein facilitating the detection of the further AHEs without using pulse oximetry.

* * * * *